United States Patent [19]

Kraus et al.

[11] Patent Number: 5,316,915
[45] Date of Patent: May 31, 1994

[54] METHOD FOR THE DETERMINATION OF ANTIBODIES AGAINST LIPOCORTINS

[75] Inventors: Michael Kraus; Jürgen Römisch, both of Marburg, Fed. Rep. of Germany

[73] Assignee: Behringwerke Aktiengesellschaft, Marburg, Fed. Rep. of Germany

[21] Appl. No.: 805,648

[22] Filed: Dec. 12, 1991

[30] Foreign Application Priority Data

Dec. 17, 1990 [DE] Fed. Rep. of Germany ....... 4040306

[51] Int. Cl.$^5$ ................. G01N 33/543; G01N 33/564
[52] U.S. Cl. ...................................... 435/7.95; 427/2; 436/506; 436/518
[58] Field of Search ....................... 435/965, 7.9, 7.92, 435/970, 7.95; 436/501, 518, 513, 817, 506; 530/389.2, 388.23; 427/2

[56] References Cited

U.S. PATENT DOCUMENTS 4,434,227  2/1984  Unger ..................................... 435/7

OTHER PUBLICATIONS

"Presence of Autoantibody for Phospholipase Inhibitory Protein, Lipomodulin, in Patients with Rheumatic Diseases", for Proc. Natl. Acad. Sci. USA, by Fusao Hirata, et al., pp. 3190–3194, May 1981.
"Autoantibodies to Recombinant Lipocortin-1 in Rheumatoid Arthritis and Systemic Lupus Erythematosus", for Annals of the Rheumatic Diseases (1989), vol. 48, pp. 843–850, by N. J. Goulding et al.
"Purification and Characterization of Six Annexins from Human Placenta" for Biol. Chem. Hoppe-Seyler, vol. 371 pp. 383–388, May 1990, by Juergen Roemisch, et al.
"Annexin Proteins PP4 and PP4-X", for Biochem. J. (1990) vol. 272 pp. 223–229, by Juergen Roemisch, et al.
"Enzyme Immunoassays in Diagnostic Medicine", for Bull World Health Organ., vol. 53, 1976, pp. 55–65, by A. Voller, et al.
Harlow, Ed *Antibodies: A Laboratory Manual* Cold Spring Harbor, N.Y., 1988 pp. 553–577, 621–622.

*Primary Examiner*—David Saunders
*Attorney, Agent, or Firm*—Finnegan, Henderson, Farabow, Garrett & Dunner

[57]  ABSTRACT

The invention relates to a method for the determination of antibodies against lipocortins (annexins) in a body fluid of a species, using proteins from the lipocortin family bound to a solid phase and using a labeled bioaffinity binding partner which is directed against single classes or a plurality of classes of immunoglobulins of this species.

18 Claims, 2 Drawing Sheets

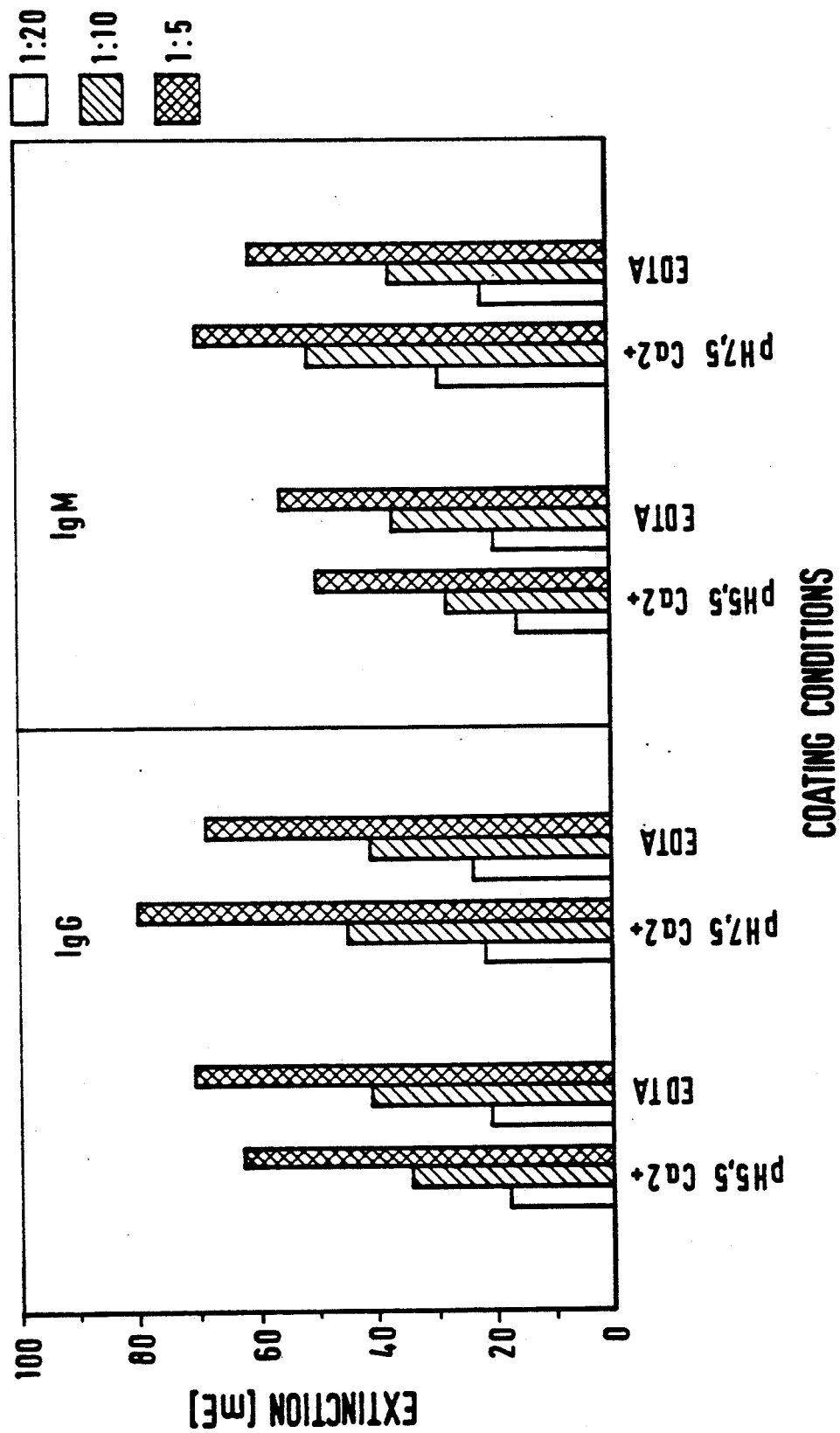

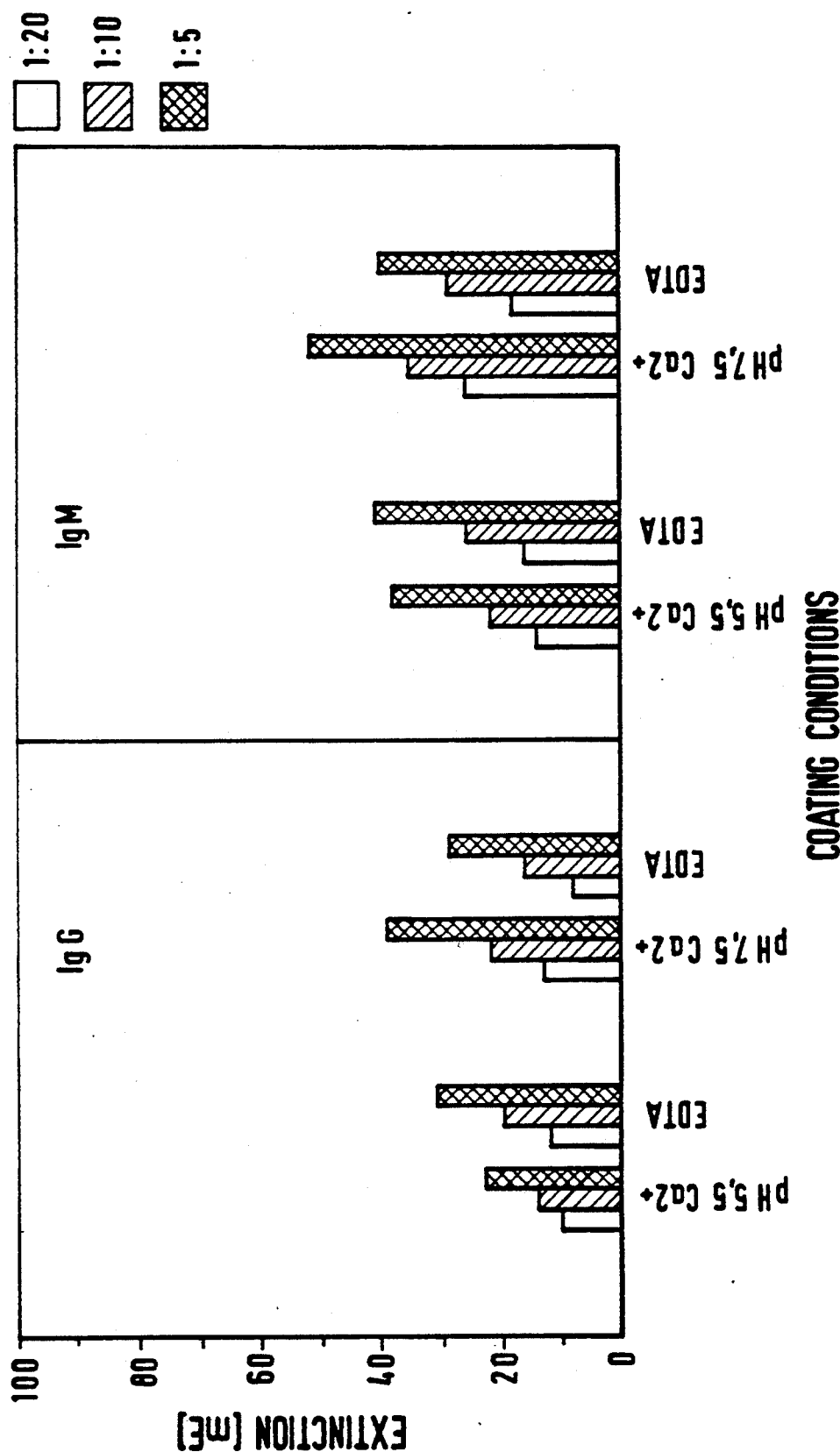

METHOD FOR THE DETERMINATION OF ANTIBODIES AGAINST LIPOCORTINS

The invention relates to a method for the determination of antibodies against lipocortins (annexins) in a body fluid of a species, using proteins from the lipocortin family bound to a solid phase and using a labeled bioaffinity binding partner which is directed against single classes or a plurality of classes of immunoglobulins of this species.

Inflammatory disorders with an autoimmunological basis are often accompanied by dysregulation of the immune system, which may lead to the production of autoantibodies which are not causally connected with the pathogenesis of the disorder. Diagnostic use of secondary antibodies of this type is possible for differential diagnosis. Secondary autoantibodies may, however, on the other hand also lead to side effects which are of importance for the therapy. Thus, the attachment of immune complexes to cell surfaces with complement binding and subsequent complement activation causes vasculitis in the vessel wall, carditis in the myocardium and glomerulonephritis in the renal tubules.

Secondary autoantibodies of this type against proteins from the lipocortin family have been described in rheumatic disorders (systemic lupus erythematosus, rheumatoid arthritis and dermatomyositis) (Hirata, F. et al., Proc. Natl. Acad. Sci. USA, 78, 3190–3194, 1981).

This lipocortin family currently comprises six very well characterized proteins which are called PP4, PP4-X, PAP III, p68, lipocortin I and II (or, in accordance with the new nomenclature, lipocortin or annexin V, IV, III, VI, I and II). Lipocortins regulate, inter alia, the release of arachidonic acid and thus the supply of mediators of inflammation—the lipocortins have an antiinflammatory effect.

Since these proteins have no leader sequence, they have been detected in relatively high concentrations especially inside cells but only in traces in body fluids. However, lipocortins have also been on cell surfaces, and it has been shown that they are also able to have an extracellular antiinflammatory effect.

However, in cases of chronic inflammation there is the risk of production of autoantibodies against lipocortins, which then lead to corticoid resistance. The determination of autoantibodies against lipocortins ought therefore to be an important criterion for deciding the choice of the type of therapy, especially on long-term use of corticoids.

A method for determining autoantibodies against lipocortin I in serum using an ELISA has been disclosed (Goulding et al., Ann. Rheum. Dis. 48, 843–850, 1989). However, this method has great disadvantages. Thus, on the one hand, only antibodies against one protein (lipocortin I) from the lipocortin family are detected. On the other hand, the sensitivity is low and the background is very high owing to non-specific binding in sera from normal subjects, so that, in particular, autoantibodies of the IgG class are scarcely detected. Finally, it has not been possible to show that sera containing rheumatoid factor, which are to be expected precisely in the indicated group of patients, are determined correctly. Hence the suitability of this method as a clinical routine screening test is low.

Hence the object was to develop a rapid immunological method which is easy to carry out for the identification of antibodies against these lipocortin proteins.

It has now been found that both the non-specific binding of antibodies to solid phases coated with lipocortins, and the effect of rheumatoid factor, in heterogeneous immunoassays can be greatly reduced by suitable coating proteins and methods, and choice of the sample buffer and conjugate buffer. Reliable diagnostic information is to be expected only when the presence of antibodies against all lipocortins is tested.

Hence the invention relates to a heterogeneous immunoassay for the determination of antibodies against lipocortins, in which a mixture of the known lipocortins is used as bioaffinity binding partner bound to the solid phase.

BRIEF DESCRIPTION OF THE DRAWINGS

FIG. 1: Effect of pH and addition of $Ca^{2+}$ during coating with PP4 on the determination of IgG and IgM anti-PP4 antibodies in a pool of human citrated plasma from normal donors. The samples were diluted 1:15 and 1:20 in a buffer system. The measurements are stated in milliextinctions.

FIG. 2: Effect on pH and addition of $Ca^{2+}$ during coating with PP4 on the determination of IgG and IgM anti-PP4 antibodies in a pool of human sera from normal donors. The samples were diluted 1:5, 1:10 and 1:20 in a buffer system. The measurements are stated in milliextinctions.

Heterogeneous enzyme immunoassays are known per se to the person skilled in the art. They can be used to detect antigens and antibodies and can be additive, such as, for example, a sandwich immunoassay, or competitive.

The bioaffinity binding partners used to detect the bound analytes are labeled, for example, with a radioisotope, with a fluorescent or chemiluminescent substance or, preferably, with an enzyme, in order to detect the binding in a known manner.

Marker enzymes for enzyme immunoassays as such are known from the literature, and alkaline phosphatase, β-galactosidase and horseradish peroxidase are preferably used, particularly preferably horseradish peroxidase.

Solid phases for heterogeneous enzyme immunoassays are known per se to the person skilled in the art, and preferably used are shaped articles such as, for example, sheet-like test elements in which the solid phase is in the form of a matrix, such as, for example, a fabric or membrane filter, or net-like, tubes, wells, beads, stars or the like and microparticles (particle size <1,000 nm) such as, for example, latex particles and magnetically attractable particles.

Particularly preferred in this context are wells in the form of microtiter plates, latex particles and magnetically attractable particles. Mjcrotiter plates are very particularly preferred.

Materials for solid phases are known to the person skilled in the art.

Preferably used as binding partners on the solid phase are proteins from the lipocortin family which are of human origin (for example as described by Romisch et al., Biol. Chem. Hoppe-Seyler 371, 383–388, 1990). Binding partners which can also be used are lipocortins prepared by genetic engineering and expressed by pro- or eukaryotic cells (see, for example, Romisch et al., Biochem. J. 272, p. 223–229 (1990)).

When carrying out heterogeneous immunoassays, various solutions known per se to the person skilled in the art are used, inter alia for washing and dilution, and these contain, inter alia, buffers, detergents and neutral proteins.

These substances are also used in the solutions which are used for the coating, including all the washing steps pertaining thereto.

Buffer systems for use in enzyme immunoassays are known to the person skilled in the art. The person skilled in the art is also aware that the nature of the buffer system used in each case depends on the pH to be obtained.

Detergents for use in solutions for heterogeneous enzyme immunoassays are likewise known to the person skilled in the art (see, for example, Voller, A. et al., Bull. World Health Organ. 53, 55–65 (1976)), and non-ionic and zwitterionic detergents are preferably used, and polyoxyethylenes are particularly preferred, and ®Tween 20 is very particularly preferred.

Neutral proteins for use in enzyme immunoassays are known to the person skilled in the art, and examples preferably used are serum albumins, gelatin, chemically modified gelatin, such as, for example, polygeline, and milk proteins such as, for example, lactoferrin; and human or bovine serum albumin, polygeline and lactoferrin are particularly preferred; and polygeline and lactoferrin are very particularly preferred.

The invention further relates to a method for coating solid phases for heterogeneous immunoassays for determining antibodies against lipocortins, where the coating is carried out with single proteins or mixtures of proteins from the lipocortin family in a pH range of 5–10, preferably in the pH range of 5–7, particularly preferably at pH 5.5.

To optimize the ratio of the signal of the pathological sample to the normal sample it is preferable to choose a particular combination of pH and additions of divalent cations.

Preferred in this connection is a method in which the coating of the solid phase is carried out using a solution, which is buffered in a range of pH 5–10, of proteins from the lipocortin family in the presence of divalent cations, specifically of $Ca^{2+}$, preferably 0.1–100 mmol/l, particularly preferably 1–10 mmol/l.

It is possible where appropriate for the proteins from the lipocortin family to be applied singly or in groups to separate solid phases, which are then incubated, separately or together, with the sample.

A preferred method entails the coating of the solid phase being carried out, as already mentioned, by binding to an antibody which is bound to the solid phase by adsorption or covalently, it being necessary that this antibody originate from a species different from that from whose body fluid antibody against the lipocortins is to be determined, in order to avoid cross-reactions with the secondary antibody which is used to label the antibodies adsorbed from the body fluid.

The properties of this secondary antibody should now be chosen so that it reacts with the antibody in the sample but not with the antibody chosen for the coating or with the lipocortins. If the intention is to determine antibodies against lipocortins in human serum, an antibody against human antibodies is suitable. It is immaterial to the invention whether the antibody is polyclonal or monoclonal. It is important that it does not cross-react with the lipocortins which have been used for the coating.

This condition is met most straightforwardly by using antibodies and lipocortins from the same species. Furthermore, a non-specific reaction of the antibody used for labeling with the antibodies used for the coating can be reduced by choosing a suitable buffer medium which preferably, apart from the buffer substances and additions such as detergents and proteins, contains antibodies which particularly preferably originate from the same species from which the antibodies used for the labeling were obtained and which do not react with the antigen used for the coating.

In connection with this optimization, the solid phase is subsequently coated in a preferred method with agents known to the person skilled in the art, preferably employing bovine serum albumin.

The labeled binding partner can be an antibody directed against individual groups of immunoglobulin classes.

A preferred method is one in which the labeled binding partner is an antibody directed against IgG, IgM or the heavy chain of IgG and IgM.

These antibodies are preferably obtained by immunization of a species, which is preferably not the species from which the body fluid originates, with immunoglobulins of the species to be investigated, and are labeled by methods known to the person skilled in the art.

The invention also relates to a method in which the body fluid to be investigated is diluted with a buffer medium which preferably contains reagents which suppress the binding of any rheumatoid factors contained in the body fluid to antibodies in this body fluid.

If human body fluids are used for the investigation, it is possible in a specific type of determination of antibodies against lipocortins to dilute samples from the IgM fraction or the total immunoglobulin fraction, which have high concentrations of rheumatoid factors (human anti-human IgG antibodies) and a high concentration of antibodies from the IgG fraction which are directed against the lipocortin(s) coated on the surface, in a buffer medium which contains suitable antibodies onto which these rheumatoid factors adsorb and are no longer able to react with the antibodies of the IgG fraction which are adsorbed onto the lipocortins.

Preferably used for this purpose as addition to the buffer medium is a globulin fraction from rabbit anti-sheep erythrocyte antibodies.

A preferred embodiment of the determination method according to the invention is as follows:

The wells of a microtiter plate are coated with a buffered solution of a mixture of lipocortins PP4, PP4-X, PAP III, lipocortin I and lipocortin II at a pH of 5 to 7 in the presence of 0.1–100 mmol/l, preferably 1–10 mmol/l, particularly preferably 5 mmol/l, $CaCl_2$. The subsequent coating is carried out with bovine serum albumin.

The coated microtiter plates can be dried and stored under suitable conditions, for example sealed in plastic-coated aluminum foil, for a lengthy period without loss of activity. For the coating, a sample or a control serum is pipetted into the wells and, after a defined incubation time, aspirated out again.

To determine the antibodies immobilized on the solid phase, a peroxidase-antibody (IgG and/or Igm) conjugate is pipetted and, after a further defined incubation time, aspirated out. To determine the bound conjugate by photometry, a substrate solution (for example OPD or TMB) is pipetted in and the reaction is stopped after a defined incubation time with sulfuric acid. The extinction is determined in a photometer. The aspiration out can be followed in each case by one or more washing steps.

In another preferred embodiment, a superparamagnetic particle is used as solid phase, and a chemiluminescent label, such as described in, for example, EP 0 330 050, is used as detection system.

The embodiments indicated in the examples are particularly preferred.

The claims also form part of the disclosure.

The following examples serve merely to illustrate the invention and restrict it in no way.

EXAMPLE 1

Coating of microtiter plates with lipocortins and the effect of various conditions on the reaction with serum and plasma from a pool from normal donors.

The lipocortin PP4 was dissolved at a concentration of 5 mg/l (lipocortins prepared by the method of Romisch et al. (1990) Biol. Chem. Hoppe-Seyler 371, 383–388) in the following buffer systems: 0.01 mol/l of acetate buffer, pH 5.5; 0.01 mol/l of HEPES (N-(2-hydroxyethyl)pipera-zine-N'-[2-ethanesulfonic acid]), pH 7.5. The solutions were mixed either with EDTA (ethylenediaminetetraacetic acid) or with $CaCl_2$ at a concentration of 0.005 mol/l. 0.125 ml was placed in each well of microtiter plates (supplied by Nunc). Incubation overnight was followed by washing several times with 0.05 mol/l tris/HCl buffer, pH 7.4, and the microtiter plates were dried in a dryer over silica gel at room temperature. After drying they were sealed air- and moisture-tight in aluminum-coated plastic bags for later use.

Human plasma and serum from a pool from normal donors was diluted in the ratio 1:5, 1:10 and 1:20 in a tris buffer (0.05 mol/l tris, PH 7.4, containing bovine serum albumin 1% (w/w), Tween 20 0.5% (w/w) and NaCl 0.045 mol/l). 0.1 ml of the previously diluted samples was pipetted into the lipocortin-coated wells of the microtiter plates and incubated at room temperature for 1 hour. This was followed by aspiration out of the solution and washing three times with buffer (for example Enzygnost washing buffer from Behringwerke, order No. OSNK). Then 0.1 ml of an antibody conjugate (for example anti-human IgG-peroxidase conjugate, batch No. 63 AP 002 A; or anti-human IgM peroxidase conjugate, batch No. 88041 A, Behringwerke, Marburg) diluted 1:51 in the above tris buffer was pipetted into each well and incubated at room temperature for 1 hour. Once again, three washes were carried out and 0.1 ml of substrate solution (for example o-phenylenediamine substrate solution, Behringwerke, order No. OSNK) was introduced into each well. After 30 min at room temperature, the reaction was stopped with 1 ml of 0.5 normal sulfuric acid in each case, and extinction at 490 nm compared with a reference wavelength of 630 nm was measured in an ELISA photometer (for example supplied by Titertek).

The extinctions determined under the various coating conditions in the determination of IgG and of IgM in serum and plasma are shown in FIG. 1 and 2 respectively. It is evident that human antibodies, both of the IgG and of the IgM type, are detectible in serum and plasma from normal donors on lipocortin-coated plates under all the coating conditions detailed above. The decrease in the signal with increasing dilution of the sample employed shows that this is attributable not to non-specific binding of the conjugate but to the adsorption of IgG and IgM from the sample. This signal, which is called background hereinafter, was more pronounced under the chosen experimental conditions in the plasma than in the serum and was higher with antibodies of the IgM type than with those of IgG type. In this example, the background for the IgG determination and for the IgM determination was always lower in the acid than in the neutral coating system. It was possible further to reduce the background in the acid medium by coating in the presence of divalent cations (for example $Ca^{2+}$).

EXAMPLE 2

Subsequent coating of the lipocortin-coated microtiter plates and effect on the background signal Microtiter plates were coated with a mixture of lipocortin I and II (5 and 1.25 mg/l respectively) as described in Example 1 at pH 5.5, 7.5 and 9.5 with the addition of 0.005 Mol/l $CaCl_2$. After several washes in 0.05 mol/l tris/HCl buffer pH 7.4, 0.125 ml of 1% (w/w) solutions of the following proteins in the buffer used for the lipocortin coating was pipetted into each well: bovine serum albumin, ovalbumin, gelatin, fetal calf serum, and 0.1% rabbit IgG and coating buffer without added protein. After incubation at room temperature for 3 hours, the microtiter plates were washed several times as described in Example 1 and dried. The background signal was determined as described in Example 1 using in each case 0.1 ml of a 1:10 dilution of a pool of human serum from normal donors.

The results in Table 1 show that the background signal can be reduced very substantially, both in the determination of antibodies of the IgG type and of the Igm type, by the nature of the coating buffer and protein chosen for the subsequent coating. In this example, BSA proved to be particularly suitable for the determination of antibodies of the IgG type, and BSA and fetal calf serum for the IgM determination.

EXAMPLE 3

Dependence of the Measured Signal on the Antigen Concentration During Coating of the Plates Microtiter plates were coated with PP4 and PP4-X in an acetate buffer (0.01 mol/l acetate, pH 5.5; 0.005 mol/l $CaCl_2$) in the following concentrations: 39, 78, 156, 313, 625, 1250, 2500 and 5000 μg/l. The subsequent coating was carried out as described in Example 2 with a 1% bovine serum albumin solution in the same acetate buffer used for the antigen coating. After the plates had been washed and dried, human serum from a pool of normal donors and pathological sera were diluted in the ratio 1:20 in a tris buffer (0.05 mol/l tris, pH 7.4, containing bovine serum albumin 3% (w/w), Tween 20 0.5% (w/w) and NaCl 0.045 mol/l). The pathological serum used for determining IgG antibodies was that of a patient with psoriasis arthropathica, and that for determining IgM antibodies was that of a patient with erythema exudativum multiforme. The bound antibodies were determined as described in Example 1.

The results, detailed in Table 2, demonstrate that a maximal reaction can be obtained, irrespective of the absolute size of the measured signal, by suitable choice of the lipocortin concentration during the coating. Under the experimental conditions chosen in this example, a saturation of the signal, both of the control and of the pathological samples, was achieved at a lipocortin concentration greater than 2 mg/l.

EXAMPLE 4

Effect of the Choice of the Buffer Solution Employed For the Sample Dilution on the Signal/Background Ratio Microtiter plates were coated with PP4 and lipocortin I/II mixture in an acetate buffer at pH 5.5 as described in Example 1, and subsequently coated with bovine serum albumin as described in Example 2. Human serum from a pool of normal donors and the serum from a patient with systemic lupus erythematosus were diluted in the ratio 1:20 in a tris buffer (0.05 mol/l tris, pH 7.4, containing bovine serum albumin 3% (w/w), Tween 20 0.5% (w/w)) and various concentrations of NaCl (0.045, 0.1, 0.2, 0.3, 0.4, 0.5, 0.6 and 0.8 mol/l). The bound antibodies of the IgG type were determined as described in Example 1.

The results presented in Table 3 demonstrate that the composition of the buffer solution employed for the sample dilution (for example addition of NaCl) may lead to a considerable reduction in the background signal, while there is less of an effect on the signal in a pathological sample. This makes it possible to achieve an optimal signal/background ratio. In this example, an optimum was reached at a concentration of about 0.3 mol/l by addition of NaCl in the determination of antibodies of the IgG type against PP4; the optimum was at about 0.2 mol/l for a mixture of lipocortin I and lipocortin II. Hence, in the optimization of an assay system for detecting antibodies against lipocortins not only is the coating of the solid phase important but also the choice of a suitable buffer for dilution and incubation of the serum on the solid phase plays a crucial part.

EXAMPLE 5

Suppression of Non-Specific Adsorption of the Anti-human Antibody-POD Conjugates to Proteins on the Solid Phase Microtiter plates were coated as described in Example 1 with PP4 and PP4-X in an acetate buffer at pH 5.5 and subsequently coated as described in Example 2 with bovine serum albumin. Human serum from a pool of normal donors and the sera from patients with systemic lupus erythematosus (for the anti-PP4 determination) and with a melanoma (for the anti-PP4-X determination) were diluted in the ratio 1:10 in a tris buffer (0.05 mol/l tris, pH 7.4, containing bovine serum albumin 3% (w/w), Tween 20 0.5% (w/w) and 0.9% NaCl). The difference from determination of the antibodies against PP4 and PP4-X described in Example 1 was that a tris buffer (0.05 mol/l tris, pH 7.4, containing bovine serum albumin 1% (w/w), Tween 20 0.5% (w/w) and NaCl 0.045 mol/l) to which various concentrations (0, 0.01, 0.02, 0.03 and 0.04% w/w) of a monoclonal antibody (for example order No. NTIDYO 80/63, Behringwerke Marburg) had been added was used for dilution of the anti-hIgG-POD and anti-hIgM-POD conjugate concentrates.

The results in Table 4 demonstrate that the signal both for the pool of normal sera and that for the pathological sera is reduced by increasing addition of mouse IgG (for example monoclonal antibody, order No. NTIDYO 80/63, Behringwerke Marburg). The ratio between the two (pathological/normal) remains approximately the same in the anti-PP4 determination, while the numerical value increases for PP4-X, but this probably results purely from the computation because of the low signal in the normal sera in this case. Thus, this example shows that non-specific interactions between the conjugated antibody and the proteins on the solid phase can be suppressed by suitable choice of additives in conjugate dilution media.

EXAMPLE 6

Suppression of False-positive IgM Determinations Caused by Rheumatoid Factors

Microtiter plates were coated as described in Example I with PP4-X in an acetate buffer at pH 5.5 and subsequently coated as described in Example 2 with bovine serum albumin. Human sera with low titers of anti-PP4-X antibodies of the IgG and IgM type (IgG−/Igm−) and high titers only of the IgG (IgG+/−Igm−) or Igm type (IgG−/IgM+) were previously diluted in the ratio 1:5 in sample buffer as described in Example 4. In a first experimental approach, the previously diluted sera were mixed with equal volumes of a serum which contained rheumatoid factors and had been diluted in various concentrations in sample buffer (for example rheumatoid factor positive control BW 18683 C. No. 12; 125 IU/ml; Behringwerke, Marburg) (final concentrations of the rheumatoid serum 1:160, 1:80, 1:40, 1:20, 1:10 and 1:5). The content of antibodies against PP4-X was determined in 0.1 ml samples of these mixtures as described in Example 1.

The results which are presented in Table 5 and which have been corrected for the measurements in the serum containing rheumatoid factors reveal that, in a human serum with a high titer of antibodies of the IgG type, "rheumatoid factor" (=anti-human IgG IgM antibodies) bound to these IgG antibodies is also detected in the IgM determination. When the titers of anti-lipocortin IgG antibodies are low ("IgG−"), the IgM determination is unaffected and independent of the titer of antilipocortin IgM antibodies ("IgM−"or "IgM+").

In a second experiment, the "IgG+/IgM−" serum which indicated falsely high IgM titers with rheumatoid factor (see Table 5) was mixed as described above with the serum containing rheumatoid factors. The final concentration of the "IgG+/IgM−" serum was 1:10, and that of the RF serum was 1:20. Dilution was carried out with the sample buffer described in Example 4, which had been mixed with various proportions (1:160 to 1:10) of a solution of the gammaglobulin fraction of rabbit anti-sheep erythrocyte antibodies (for example Ambo-zeptor for Rapitex reagents, No. 62 MH, batch 08, Behringwerke, Marburg). The IgM titers were determined as described above.

The results, which are likewise shown in Table 5, demonstrate that the falsely high IgM determinations owing to binding of rheumatoid factor to IgG on the solid phase can be neutralized by adding a solution of a gammaglobulin fraction to the medium used for the sample dilution.

EXAMPLE 7

Screening of Sera Using a Solid Phase Coated With All Lipocortins

A panel of human sera from normal donors and from patients with autoimmunological and/or inflammatory disorders was tested as described in Example 6 in dilutions of 1:10 for antibodies of the IgG and IgM type against lipocortins. The microtiter plates were coated as described in Example 1 with PP4, PP4-X, PAP III, p68 and lipocortin I/II mixture, and with a mixture of all lipocortins at a concentration of 5 mg/l (lipocortin II: 1.25 mg/l), and subsequently coated as described in Example 2 with bovine serum albumin.

The results of the determinations of the IgG and IgM anti-lipocortin antibodies in sera from 114 normal blood donors are listed in Table 6. The list shows the frequency of the measurements found in classes which are divided logarithmically (in milliextinctions). The means and median of each of the distributions agree well but differ for each coating antigen.

Among 123 samples from patients with autoinumunological and/or inflammatory disorders, 69 were found to have titers of antibodies against lipocortins of the IgG or IgM type above the 90% interval of the "normal distribution" determined in each case above, and these are called "positive" hereinafter. It emerged that 38 patients had produced antibodies of the IgG type and 25 patients had produced those of the IgM type, these reacting with only one lipocortin. The specificity was distributed over all the lipocortins (see Table 7). This shows that only comprehensive screening with all lipocortins and against both antibody types is able to detect disturbances of the function of the lipocortins caused by anti-lipocortin antibodies.

43 positive samples were also tested on a microtiter plate coated with all lipocortins. This revealed "positivity" in 13/20 with IgG and 7/15 with IgM antibodies (see Table 7). This example thus demonstrates that a solid phase coated with all lipocortins is suitable for a general method for screening samples for antibodies both of the IgG and of the IgM type against single lipocortins and against several lipocortins.

TABLE 1

Effect of the subsequent coating of microtiter plates coated with lipocortin I/II mixture on the IgG and IgM determination in a pool of human sera from normal donors (Example 2).
Used for the subsequent coating were 1% solutions of bovine serum albumin (BSA), ovalbumin (OA), gelatin (G), fetal calf serum (FCS), and 0.1% rabbit IgG (RI) and coating buffer without addition (−) of protein with pH values of 5.5, 7.5 and 9.5. The serum was diluted 1:10 in buffer for use. The measurements are stated in milliextinctions; Ab = antibody class.

| Protein | pH for subsequent coating | | | Ab |
|---|---|---|---|---|
| | 5.5 | 7.5 | 9.5 | |
| | | | | IgG |
| — | 18 | 29 | 24 | |
| BSA | 10 | 17 | 20 | |
| OA | 250 | 126 | 92 | |
| G | 21 | 22 | 19 | |
| FCS | 38 | 55 | 45 | |
| RI | 24 | 12 | 36 | |
| | | | | IgM |
| — | 70 | 86 | 93 | |
| BSA | 64 | 74 | 78 | |
| OA | 73 | 85 | 87 | |
| G | 111 | 107 | 99 | |
| FCS | 56 | 84 | 90 | |
| RI | 301 | 160 | 131 | |

TABLE 2

Dependence of the anti-PP4 and -PP4-X IgG and IgM determination in sera from normal blood donors (N) and from patients with autoimmune diseases (P) on the concentration of the coating antigen. The measurements are stated in milliextinctions (Example 3).

| Concentration | Coating antigen | | | | |
|---|---|---|---|---|---|
| | PP4 | | PP4-X | | |
| [mg/l] | N | P | N | P | Ab class |
| 0.04 | 63 | 92 | 69 | 104 | IgG |
| 0.08 | 53 | 101 | 70 | 101 | |
| 0.16 | 50 | 93 | 71 | 101 | |
| 0.31 | 62 | 96 | 86 | 109 | |
| 0.63 | 78 | 120 | 110 | 136 | |
| 1.25 | 122 | 166 | 139 | 165 | |
| 2.5 | 142 | 187 | 180 | 207 | |
| 5.0 | 152 | 201 | 185 | 208 | |
| 0.04 | 10 | 119 | 23 | 64 | IgM |
| 0.08 | 25 | 64 | 22 | 64 | |
| 0.16 | 22 | 65 | 26 | 67 | |
| 0.31 | 25 | 72 | 29 | 77 | |
| 0.63 | 28 | 72 | 35 | 94 | |
| 1.25 | 37 | 97 | 46 | 149 | |
| 2.5 | 42 | 118 | 62 | 178 | |
| 5.0 | 46 | 129 | 63 | 207 | |

TABLE 3

Effect of NaCl in the sample dilution buffer on the determination of antibodies of the IgG type against PP4 and lipocortin I/II mixture (L I/II) in a pool of sera from normal donors (normal sera) and a serum from a patient with systemic lupus erythematosus (pathoserum). The measurements are stated in milliextinctions (Example 4).

| NaCl concentration | Extinction (490 nm–630 nm) | | | | Normal sera/ pathosera ratio | |
|---|---|---|---|---|---|---|
| | Normal sera | | Pathoserum | | | |
| [mol/l] | PP4 | L I/II | PP4 | L I/II | PP4 | L I/II |
| 0.045 | 194 | 152 | 627 | 848 | 3.2 | 2.5 |
| 0.1 | 106 | 11 | 549 | 791 | 5.2 | 3.1 |
| 0.2 | 62 | 85 | 406 | 587 | 6.5 | 3.3 |
| 0.3 | 40 | 76 | 270 | 439 | 6.8 | 3.0 |
| 0.4 | 37 | 64 | 180 | 352 | 4.9 | 2.6 |
| 0.5 | 36 | 62 | 132 | 282 | 3.7 | 2.1 |
| 0.6 | 38 | 61 | 95 | 218 | 2.5 | 1.6 |
| 0.8 | 33 | 49 | 79 | 134 | 2.4 | 1.5 |

TABLE 4

Effect of a monoclonal antibody in the conjugate dilution buffer on the determination of IgG antibodies against PP4 and PP4-X in a pool of human sera from normal donors (normal sera) and from patients with systemic lupus erythematosus (PP4) and with a melanoma (PP4-X) (pathosera). The measurements are stated in milliextinctions (Example 5).

| MAb concentration | Extinction (490 nm–630 nm) | | | | Normal sera/ pathosera ratio | |
|---|---|---|---|---|---|---|
| | Normal sera | | Pathoserum | | | |
| [mol/l] | PP4 | PP4-X | PP4 | PP4-X | PP4 | PP4-X |
| 0 | 169 | 64 | 585 | 336 | 3.5 | 5.3 |
| 0.01 | 75 | 20 | 246 | 209 | 3.3 | 10.3 |
| 0.02 | 58 | 13 | 181 | 168 | 3.1 | 13.1 |
| 0.03 | 49 | 9 | 184 | 152 | 3.7 | 16.3 |
| 0.04 | 40 | 6 | 132 | 134 | 3.3 | 22.9 |

TABLE 5

Suppression of false-positive IgM determinations caused by rheumatoid factor. Sera with low titers of anti-PP4-X antibodies of the IgG and IgM type (IgG-/IgM-) and high titers only of the IgG (IgG+/IgM-) or IgM type (IgG-/IgM+), and sample buffer were mixed with various amounts of a human serum containing rheumatoid factor (125 IU/ml). The IgG and IgM determination without additions, the measurements of the IgM determination after addition of rheumatoid factor serum, and on addition of various amounts of a gamma-globulin solution from rabbits to a serum with a false positive reaction with rheumatoid factor are listed. The measurements are stated in milliextinctions (Example 6).

|  | IgG-/IgM- | IgG+/IgM- | IgG-/IgM+ |
|---|---|---|---|
| Measurements without addition [mE] | | | |
| IgG | 43 | 721 | 37 IgM |
| 37 | 91 | 228 | |
| IgM determination with the addition of RF serum | | | |
| 1:160 | 26 | 93 | 200 |
| 1:80 | 42 | 105 | 208 |
| 1:40 | 32 | 111 | 231 |
| 1:20 | 34 | 149 | 250 |
| 1:10 | 24 | 176 | 215 |
| 1:5 | 18 | 201 | 209 |
| IgM determination with the addition of gamma-globulin solution | | IgG+/IgM- + RF serum (1:20) | |
| without | | 157 | |
| 1:160 | | 147 | |
| 1:80 | | 126 | |
| 1:40 | | 140 | |
| 1:20 | | 111 | |
| 1:10 | | 112 | |

TABLE 6

Statistical analysis of the distribution of titers of antibodies of the IgG and IgM type against single lipocortins and against mixtures of lipocortins in a panel of sera from normal donors (n = 114) in classes divided logarithmically (milliextinctions) (Example 7).

|  | PP4 | PP4-X | PAP III | p68 | LI/II | PP4-LII |
|---|---|---|---|---|---|---|
| IgG type: | | | | | | |
| Number | 114 | 114 | 114 | 114 | 114 | 114 |
| Mean | 42 | 76 | 47 | 80 | 46 | 58 |
| Median | 39 | 67 | 41 | 78 | 49 | 53 |
| 90% interval | 90 | 117 | 105 | 193 | 109 | 112 |
| IgM type: | | | | | | |
| Number | 114 | 114 | 114 | 114 | 114 | 114 |
| Mean | 41 | 70 | 43 | 59 | 62 | 58 |
| Median | 40 | 69 | 43 | 61 | 63 | 61 |
| 90% interval | 93 | 154 | 98 | 141 | 136 | 126 |

TABLE 7

Occurrence of antibodies of the IgG and IgM type against lipocortins in sera from patients with autoimmunological and/or inflammatory disorders. Samples classified as positive were those whose antibody titers are above the 90% interval of the particular distribution of the measurements on normal donors (see Table 6 and 7). PP4-LII designates the results of the investigation of some of these samples on a microtiter plate coated with all lipocortins; L I/II = lipocortin I and lipocortin II mixture (Example 7).
Total number of patients: 123
of whom positive (IgG and/or IgM type): 69
of whom found positive in each case:

| Antibody type | Antigen | | | | | |
|---|---|---|---|---|---|---|
|  | PP4 (Σ = 69) | PP4-X | PAP III | p68 | L I/II | PP4-LII (Σ = 43) |
| IgG | 16%(11) | 15% (10) | 10%(7) | 2%(1) | 13% (9) | 30%(13) |
| IgM | 4% (3) | 4% | 7%(5) | 2%(1) | 19% | 16% (7) |

TABLE 7-continued

Occurrence of antibodies of the IgG and IgM type against lipocortins in sera from patients with autoimmunological and/or inflammatory disorders. Samples classified as positive were those whose antibody titers are above the 90% interval of the particular distribution of the measurements on normal donors (see Table 6 and 7). PP4-LII designates the results of the investigation of some of these samples on a microtiter plate coated with all lipocortins; L I/II = lipocortin I and lipocortin II mixture (Example 7).
Total number of patients: 123
of whom positive (IgG and/or IgM type): 69
of whom found positive in each case:

| Antibody type | Antigen | | | | | |
|---|---|---|---|---|---|---|
|  | PP4 (Σ = 69) | PP4-X | PAP III | p68 | L I/II | PP4-LII (Σ = 43) |
|  |  |  | (3) |  |  | (13) |

We claim:

1. A heterogeneous immunoassay method for determining IgX antibodies directed against lipocortins, wherein X may be any of the known Ig-classes, comprising the steps of:
    a) fixing a mixture of two or more purified known lipocortions to a solid support;
    b) contacting a sample of a body fluid with the solid support to form an antigen-IgX complex on the solid support, wherein the lipocortin antigen of the antigen-IgX complex is fixed to the solid support of step a) and the IgX of the antigen-IgX complex is from the body fluid of step b);
    c) removing unbound sample;
    d) treating the antigen-IgX complex with a labeled Ig-class specific antibody or a mixture of labeled Ig-class specific antibodies; and
    e) determining the amount of label bound to the solid support via antigen-IgX-labeled antibody complex as a measure of the IgX content of the sample.

2. The immunoassay method of claim 1, wherein the lipocortins are selected from the group consisting of PP4, PP4-X, PAP III, p68,lipocortin I and II.

3. The immunoassay of claim 1, wherein the lipocortins are from the lipocortin family from the same species from which the sample of a body fluid is derived.

4. The immunoassay of claim 1, wherein in the lipocortins are bound to the solid support using a solution which is buffered in the pH range from 5.5 to 9.5.

5. The immunoassay of claim 4, wherein CaCl$_2$ is added during step a).

6. The immunoassay of claim 4, wherein the range of pH of the solution used in step a) is from 5.5 to 7.5.

7. The immunoassay of claim 1, wherein the sample of body fluid is diluted in a medium containing a gamma-globulin fraction from a rabbit, which has been immunized against sheep erythrocytes.

8. The immunoassay of claim 1, wherein the label is an enzyme.

9. The immunoassay of claim 8, wherein the enzyme is peroxidase.

10. A method of preparing a solid-phase carrier for use in a heterogeneous immunoassay method for determining IgX antibodies directed against lipocortins, wherein X may be any of the known Ig-classes, comprising the steps of:
    incubating a solid support with a mixture of lipocortins in pH range from 5.5 to 9.5 in the presence of CaCl; and washing to remove unbound lipocortins.

11. A heterogeneous immunoassay method for determining IgX antibodies directed against lipocortins, wherein X may be any of the known Ig-classes, comprising the steps of:
 a) fixing one or more purified known lipocortins to a solid support;
 b) contacting a sample of a body fluid with the solid support to form an antigen-IgX complex on the solid support, wherein the lipocortin antigen of the antigen-IgX complex is fixed to the solid support of step a) and the IgX of the antigen-IgX complex is from the body fluid of step b);
 c) removing unbound sample;
 d) treating the antigen-IgX complex with a labeled Ig-class specific antibody or a mixture of labeled Ig-class specific antibodies; and
 e) determining the amount of label bound to the solid support via antigen-IgX-labeled antibody complex as a measure of the IgX content of the sample.

12. The immunoassay of claim 11, wherein the lipocortins are selected from the group consisting of PP4, PP4-X, PAP III, p68, lipocortin I and II.

13. The immunoassay of claim 11, wherein the lipocortins are from the lipocortin family from the same species from which the sample of a body fluid is derived.

14. The immunoassay of claim 11, wherein the sample of body fluid is diluted in a medium containing a gamma-globulin fraction from a rabbit, which has been immunized against sheep erythrocytes.

15. The immunoassay of claim 11, wherein the label is an enzyme.

16. The immunoassay of claim 15, wherein the enzyme is peroxidase.

17. THe immunoassay of claim 11, wherein the range of pH of the solution used in step a) is from 5.5 to 7.5.

18. A method of preparing a solid-phase carrier for use in a heterogeneous immunoassay method for determining IgX antibodies directed against lipocortins, wherein X may be any of the known Ig-classes, comprising the step of:
 incubating a solid support with a single lipocortin in pH range from 5.5 to 9.5 in the presence of $CaCl_2$ washing to remove unbound lipocortins.

* * * * *

UNITED STATES PATENT AND TRADEMARK OFFICE
CERTIFICATE OF CORRECTION

PATENT NO. : 5,316,915
DATED : May 31, 1994
INVENTOR(S) : Michael KRAUS et al.

It is certified that error appears in the above-indentified patent and that said Letters Patent is hereby corrected as shown below:

Claim 1, column 12, line 25 change "lipocortions" to --lipocortins--.

Claim 4, column 12, line 45 after "in" insert --step a)--.

Claim 10, column 12, line 68 change "CaCl" to --$CaCl_2$--.

Claim 11, column 13, line 7 between "support" and ";" insert --by incubation in a solution which is buffered in the pH range from 5.5 to 9.5 in the presence of $CaCl_2$--.

Claim 17, column 14, line 13 change "THe" to --The--.

Claim 18, column 14, line 19 change "step" to --steps--.

UNITED STATES PATENT AND TRADEMARK OFFICE
CERTIFICATE OF CORRECTION

PATENT NO. : 5,316,915
DATED : May 31, 1994
INVENTOR(S) : Michael KRAUS et al.

It is certified that error appears in the above-indentified patent and that said Letters Patent is hereby corrected as shown below:

Claim 18, column 14, line 21 after "$CaCl_2$" insert --; and--.

Signed and Sealed this

Twenty-first Day of March, 1995

Attest:

BRUCE LEHMAN

Attesting Officer

Commissioner of Patents and Trademarks